United States Patent [19]
Bauer

[11] Patent Number: 5,951,489
[45] Date of Patent: Sep. 14, 1999

[54] BIOPSY SURGICAL APPLIANCE

[75] Inventor: Alberto Bauer, Santa Domingo, Dominican Rep.

[73] Assignee: Allegiance Healthcare Corporation, McGaw Park, Ill.

[21] Appl. No.: 09/153,541

[22] Filed: Sep. 16, 1998

Related U.S. Application Data

[63] Continuation of application No. 08/781,780, Jan. 9, 1997, abandoned.

[51] Int. Cl.⁶ .................................................. A61B 5/00
[52] U.S. Cl. .................................................... 600/567
[58] Field of Search ........................... 600/562, 564–567; 606/167, 170

[56] References Cited

U.S. PATENT DOCUMENTS

| | | | |
|---|---|---|---|
| 4,924,878 | 5/1990 | Nottke | 128/751 |
| 4,958,625 | 9/1990 | Bates et al. | 128/754 |
| 5,243,994 | 9/1993 | Ranalletta | 128/754 |
| 5,282,476 | 2/1994 | Terwilliger | 128/753 |
| 5,284,156 | 2/1994 | Schramm et al. | 128/754 |

FOREIGN PATENT DOCUMENTS

| | | |
|---|---|---|
| 0 536 888 A1 | 4/1993 | European Pat. Off. . |
| WO 91/01112 | 2/1991 | WIPO . |

*Primary Examiner*—Max Hindenburg
*Attorney, Agent, or Firm*—Karl F. Ross; Paul E. Schaafsma

[57] ABSTRACT

A biopsy surgical appliance includes a stylet slider sliding in a longitudinal plane and placed laterally with respect to a longitudinal axis, a cannula slider sliding in a longitudinal plan placed laterally with respect to the axis of a needle and not interfering in the operative framework of stylet slider, holding/releasing device made up of a first independent hooking/releasing device for stylet slider, a second independent hooking/releasing device for cannula slider, two independent single control push-buttons of which the first one acts on the first hooking/releasing device and the second one is of the progressive type and acts in progression on said first hooking/releasing device at the first device if it has not been released yet and then on the second hooking/releasing device.

14 Claims, 17 Drawing Sheets

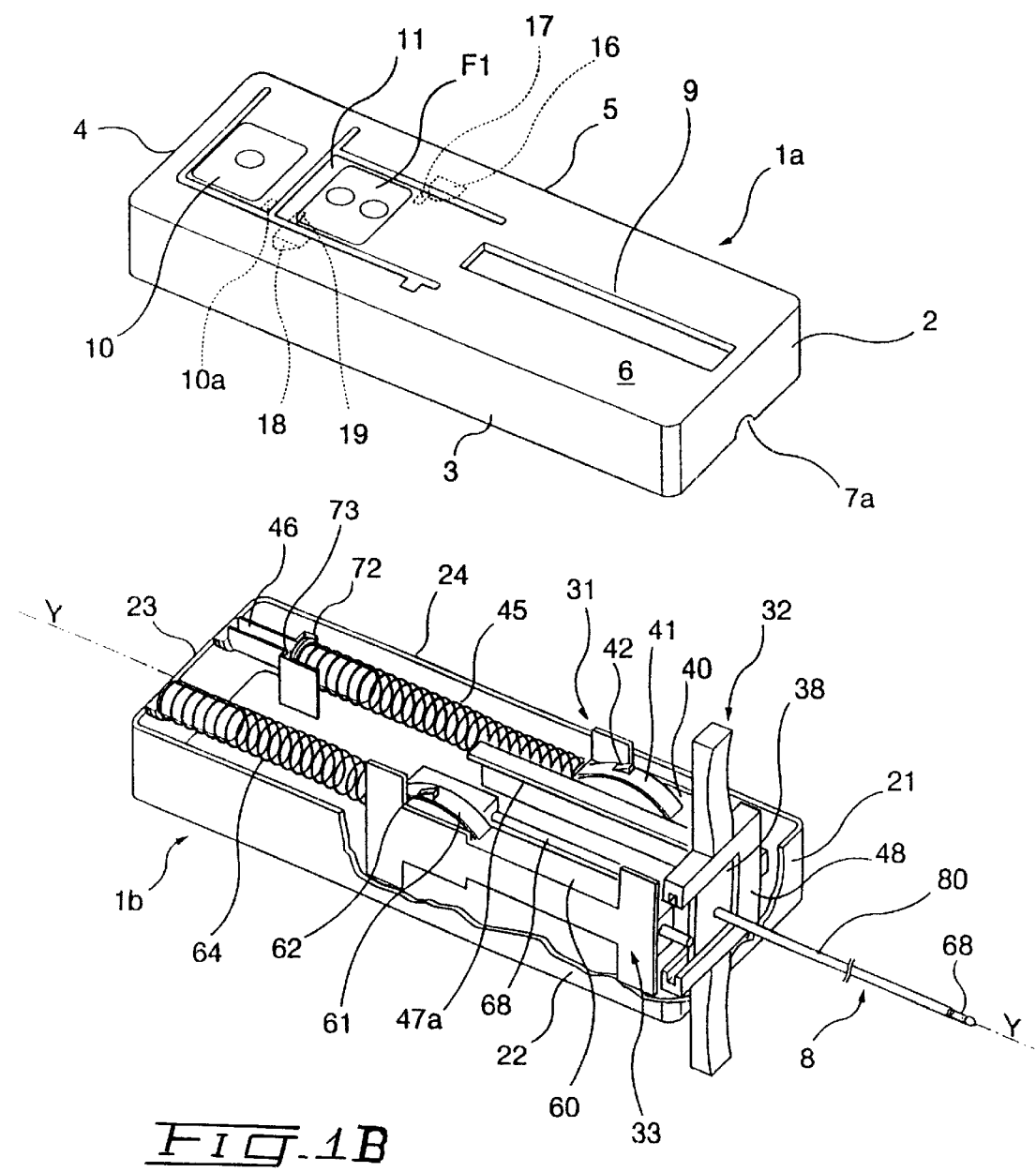

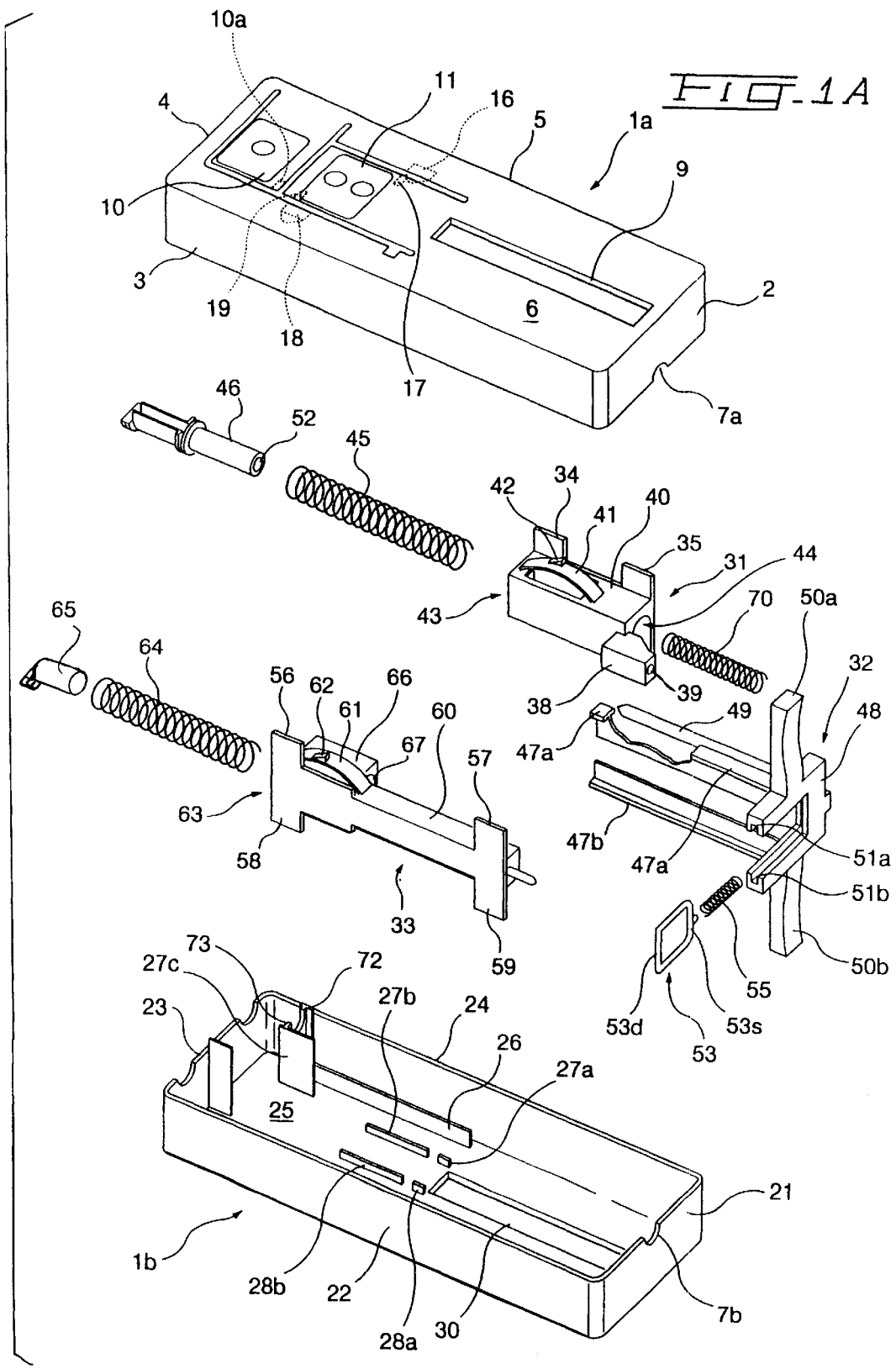

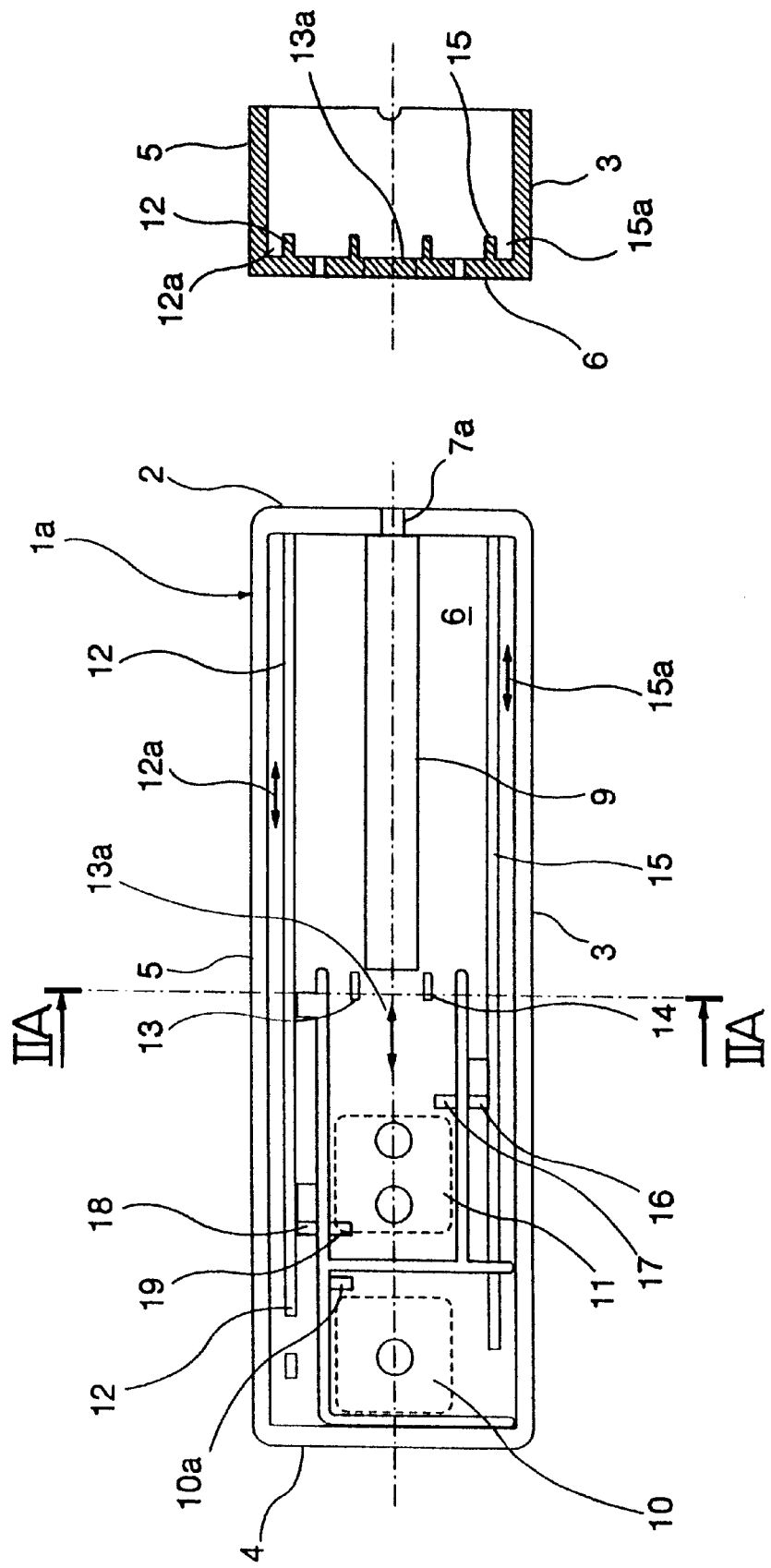

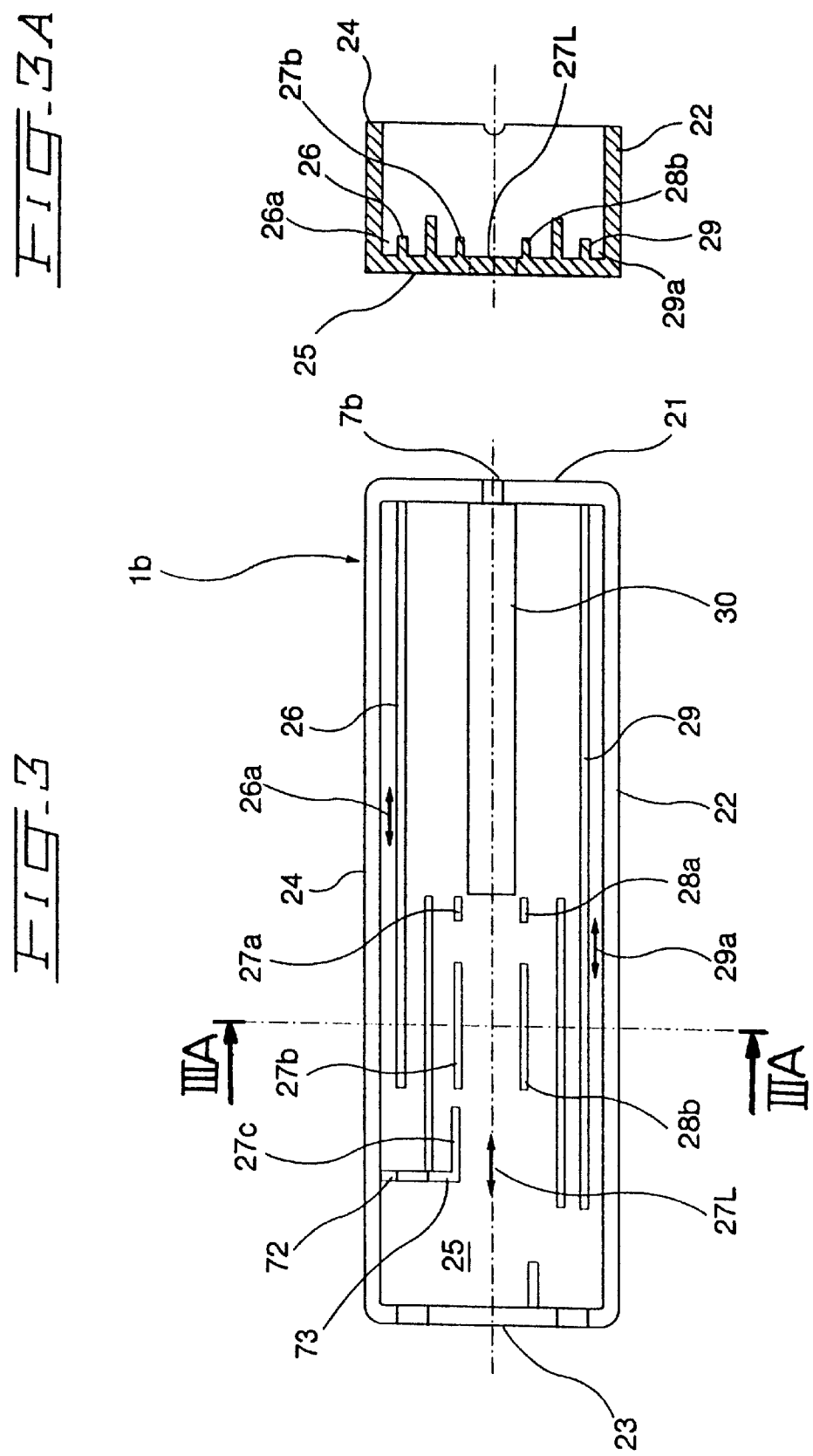

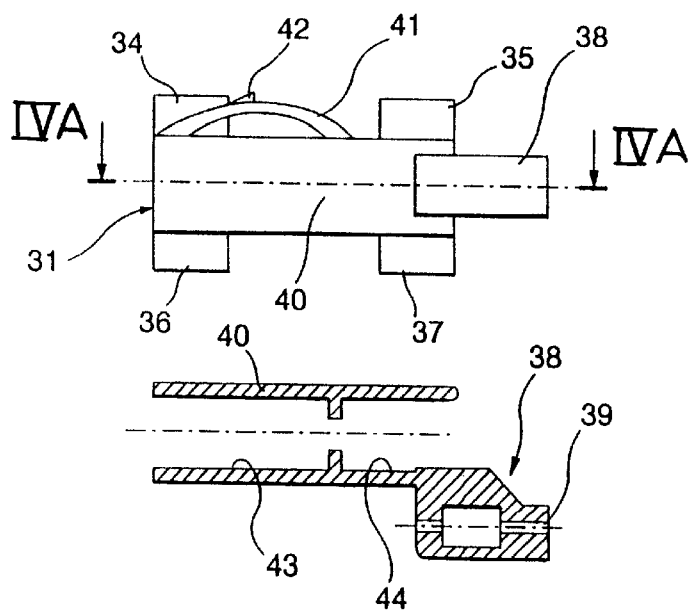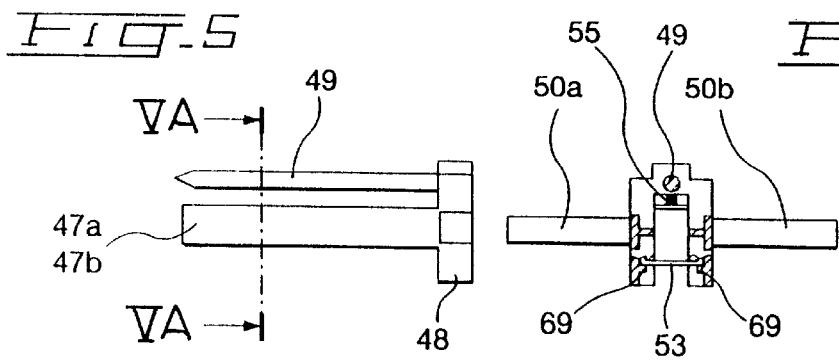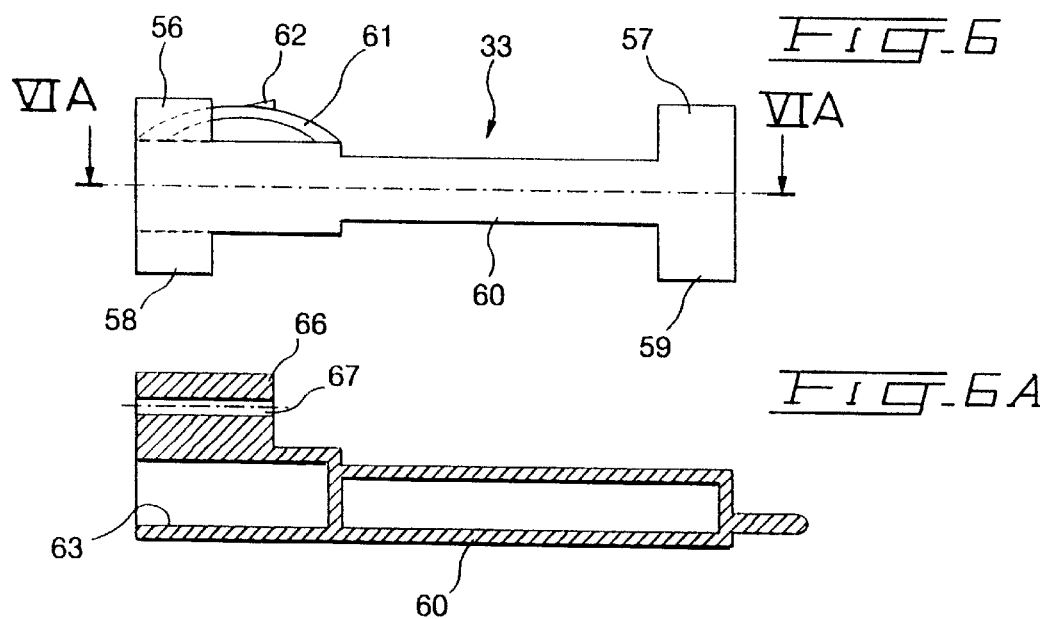

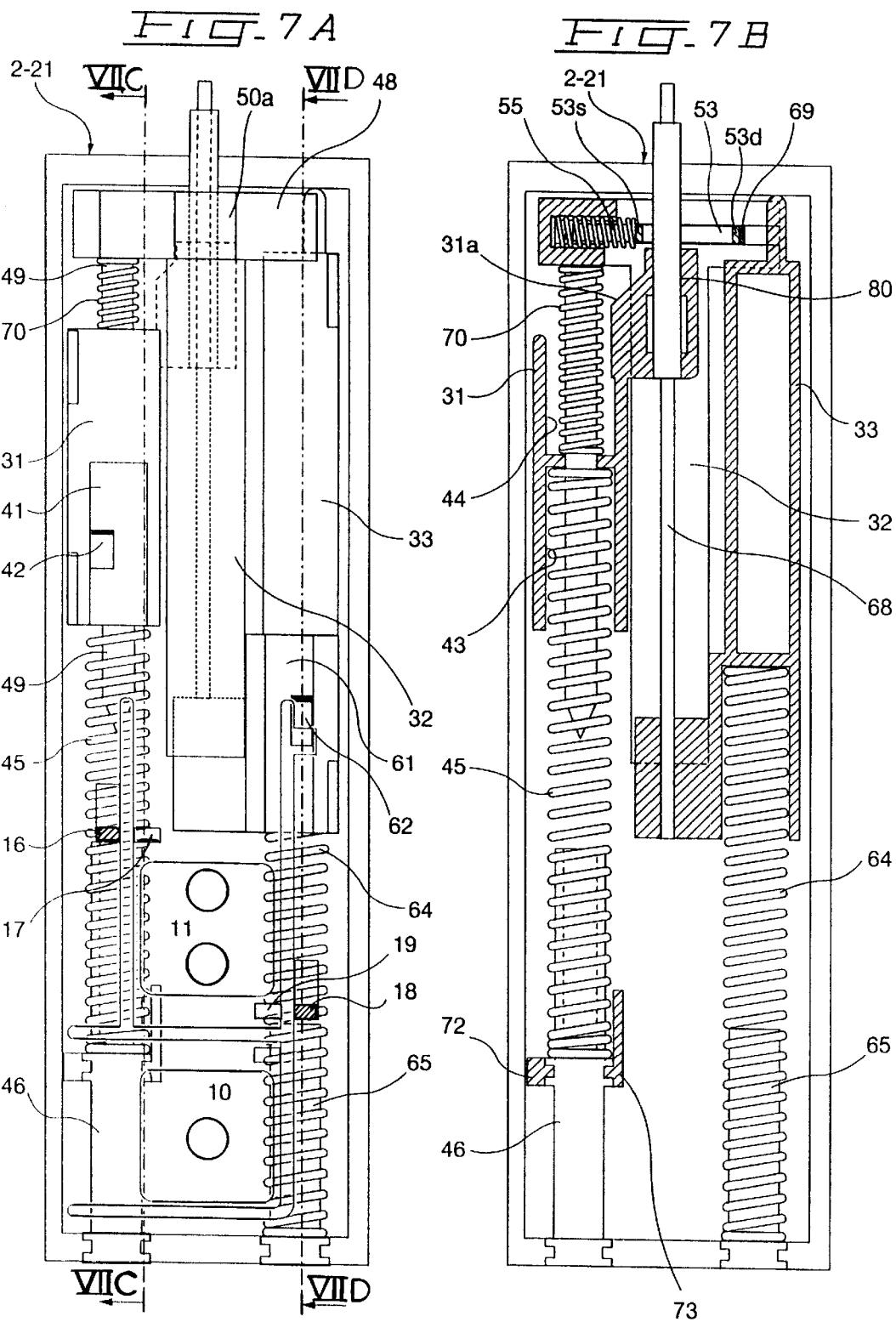

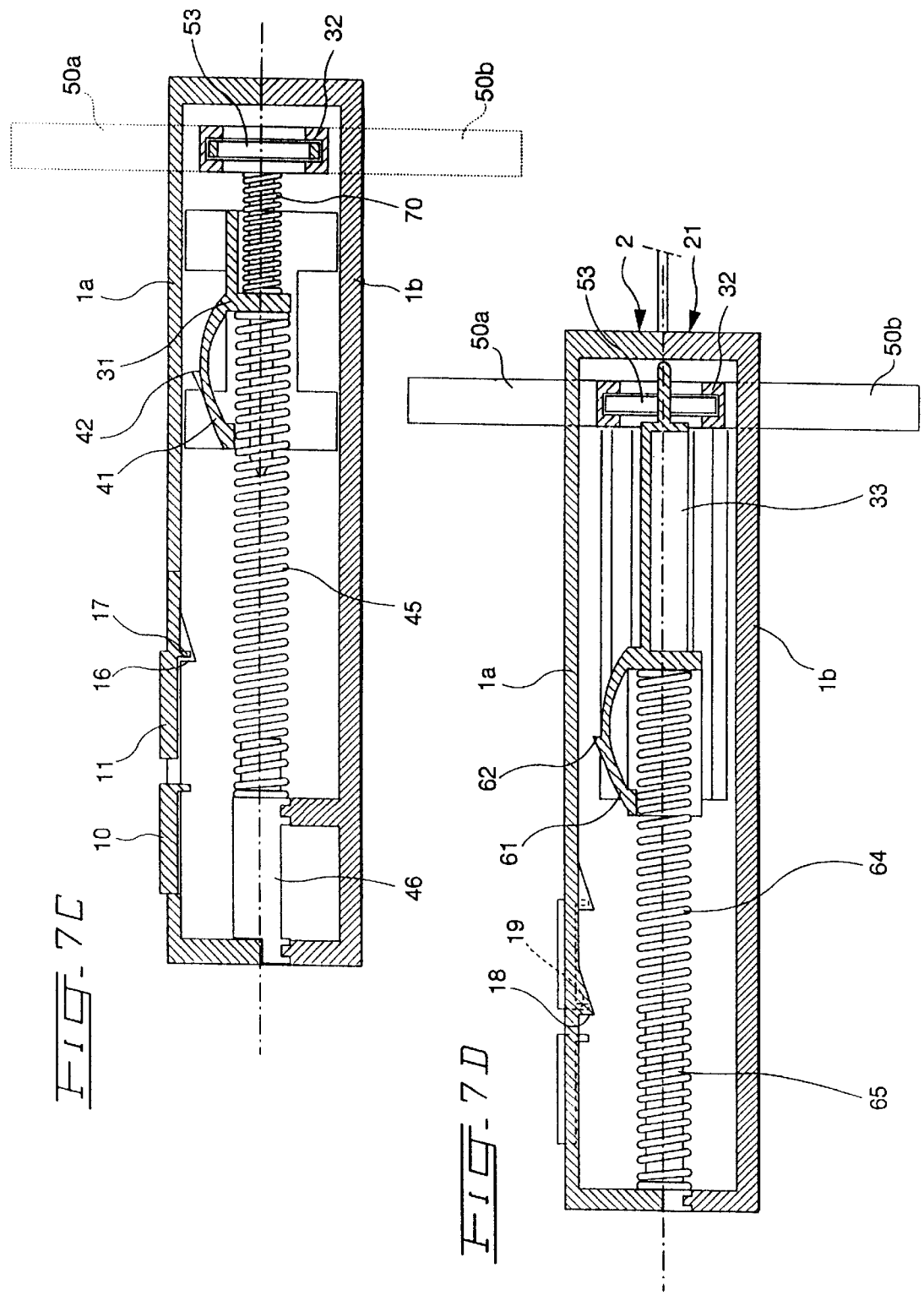

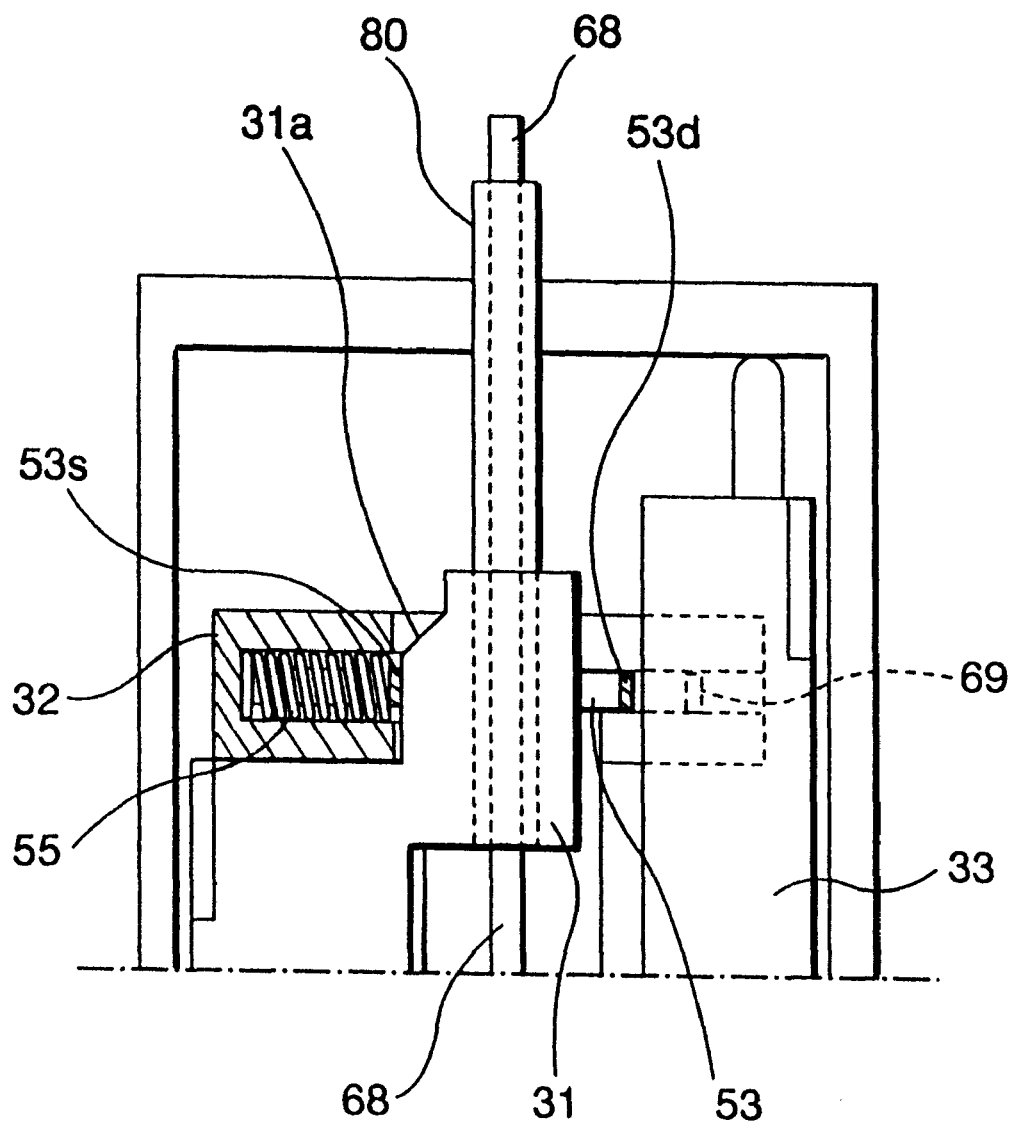

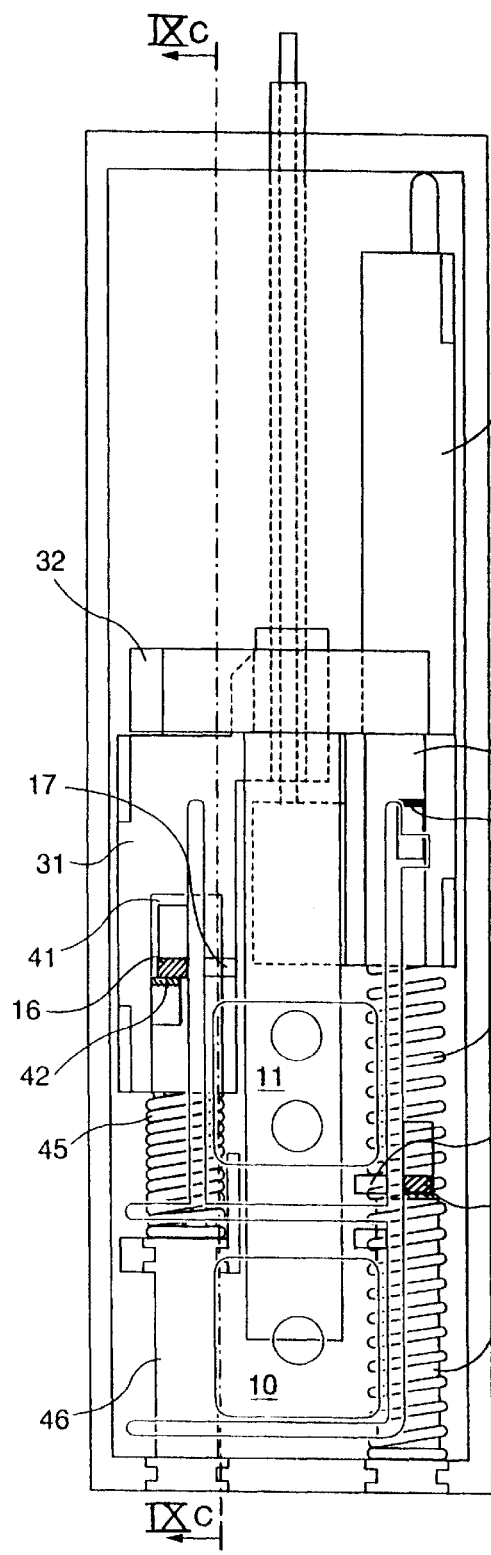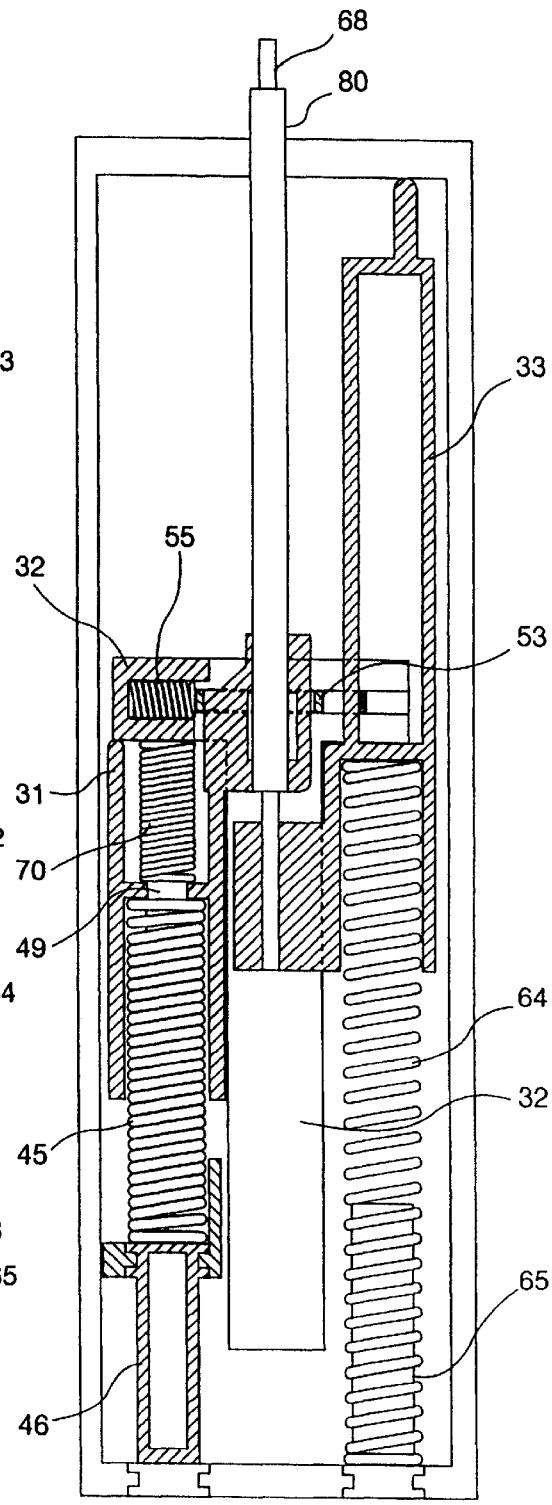

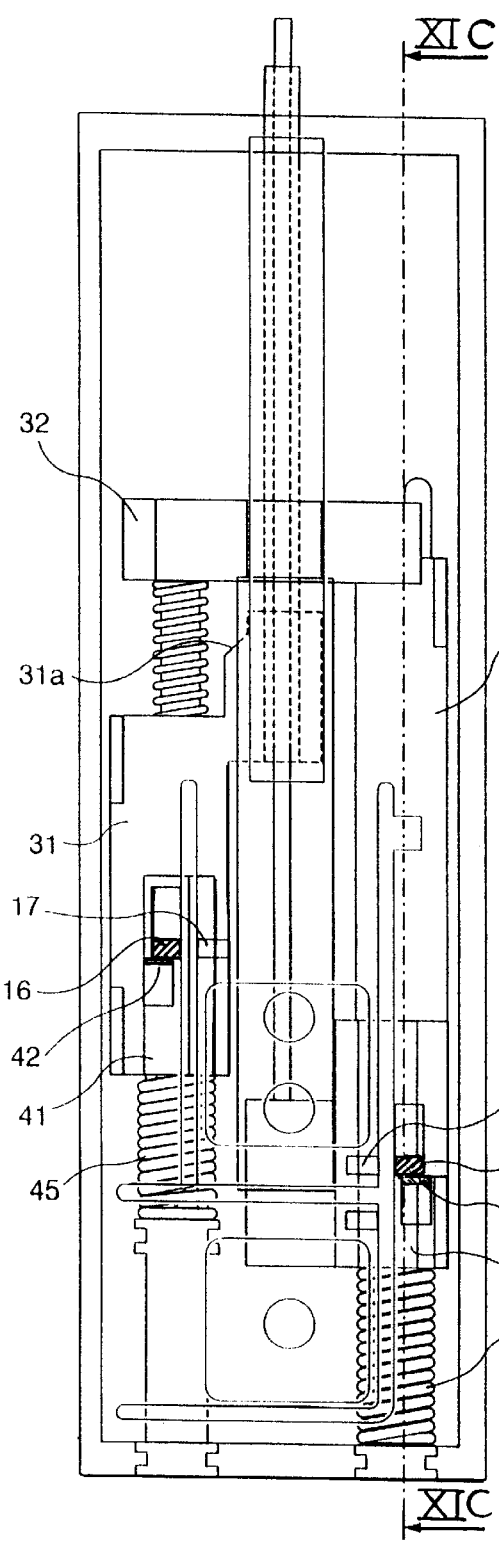
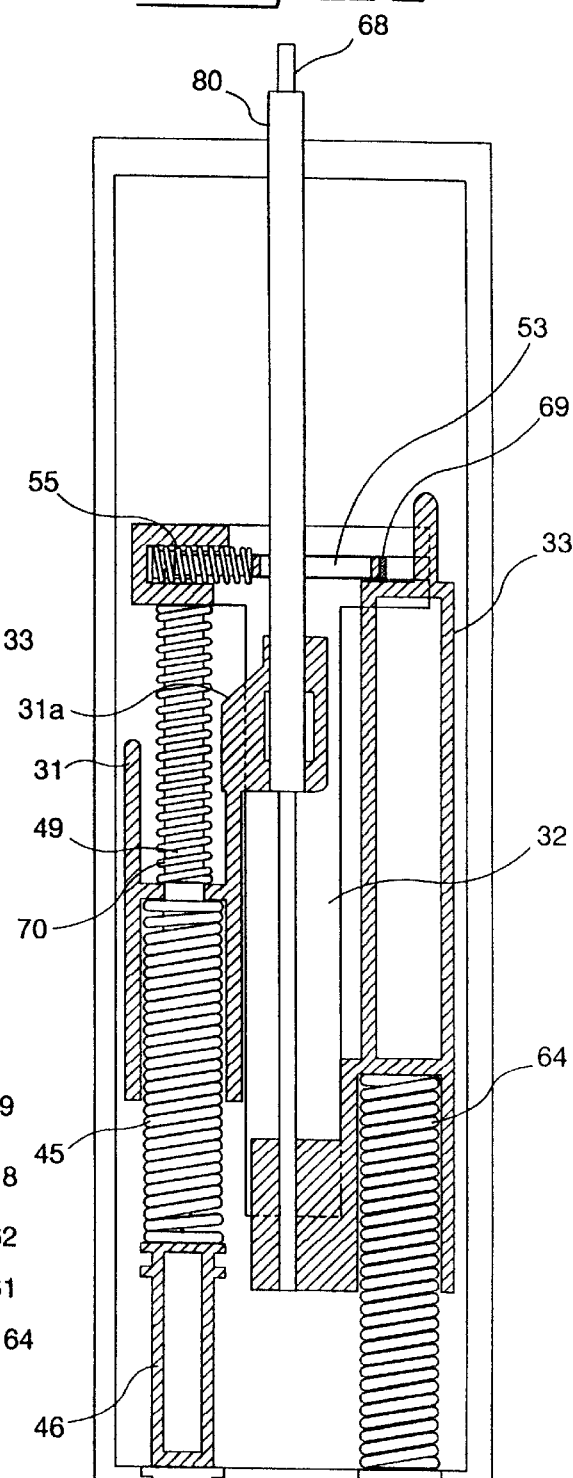

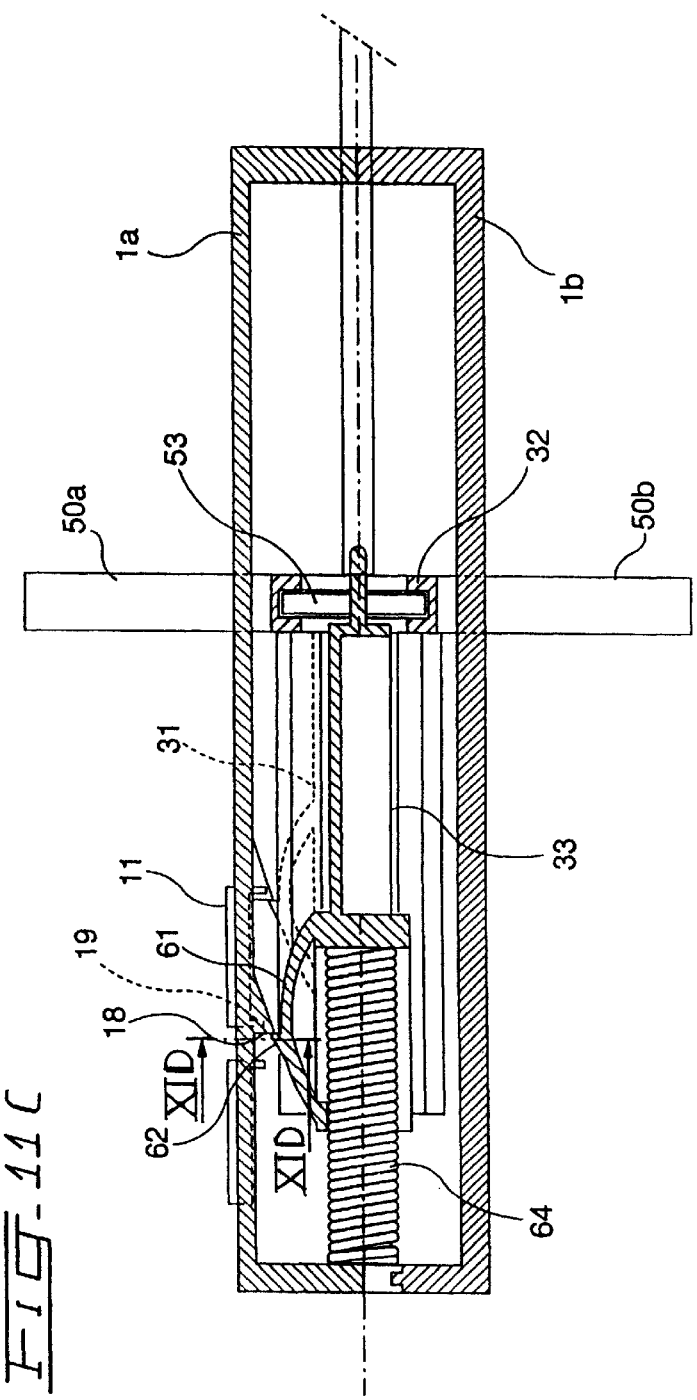
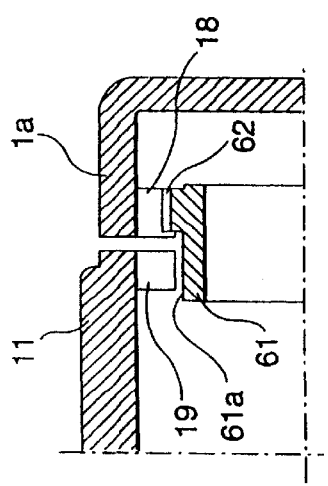
FIG. 11D
FIG. 11C

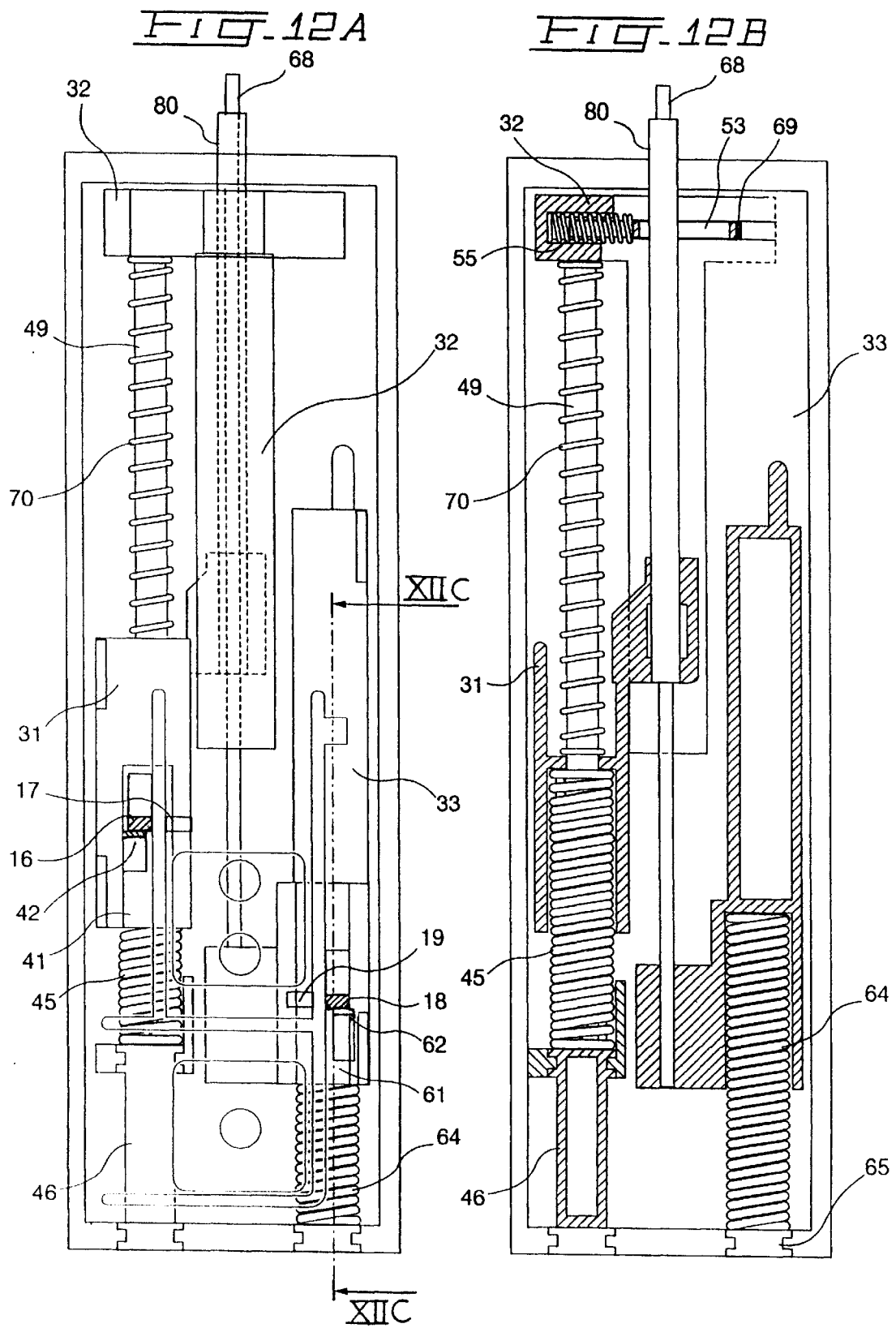

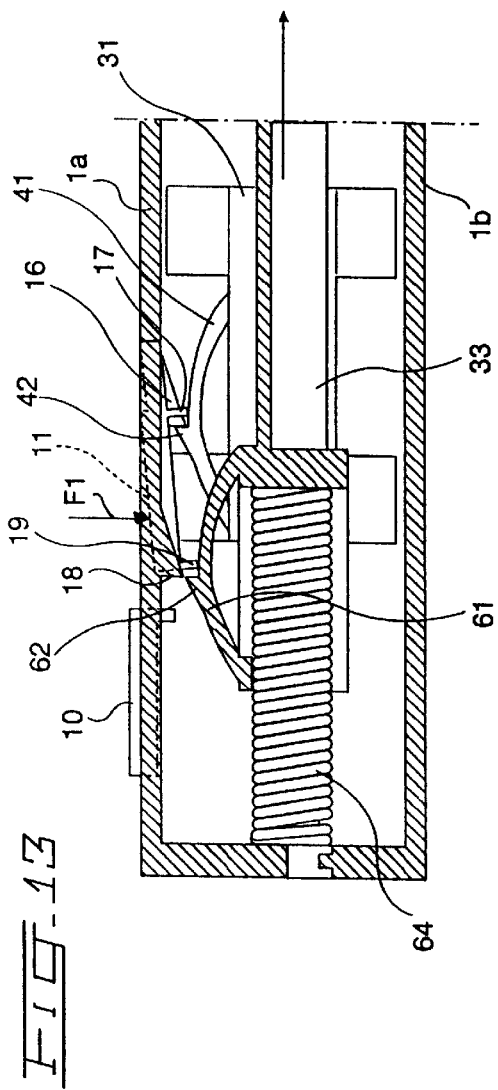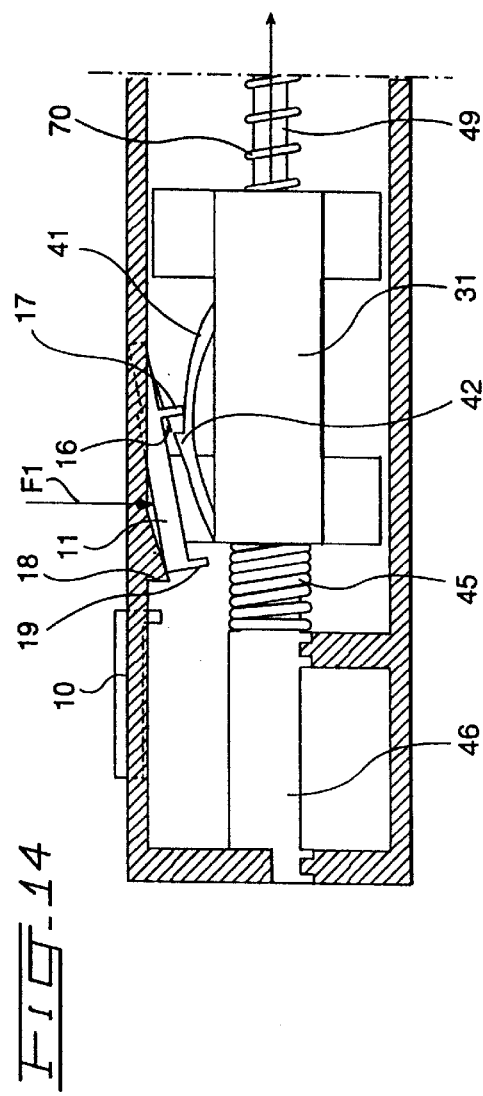

BIOPSY SURGICAL APPLIANCE

CROSS REFERENCE TO RELATED APPLICATION

This application is a continuation of application Ser. No. 08/781,780 filed Jan. 9, 1997 now abandoned.

FIELD OF THE INVENTION

The present invention relates to a biopsy surgical appliance used to remove a sample of body tissue in order to be able to examine it while causing the least possible damage to the patient subject to removal.

BACKGROUND OF THE INVENTION

Many biopsy surgical appliances are currently known. They substantially include a needle made up of a thin probe ending with a stylet arranged coaxially inside a hollow circular element acting as a cannula, and a control device for needle operation.

With reference to patent U.S. Pat. No. 4,958,625, no device includes two sliders, aligned on the same needle axis, elastically loadable through a respective spring, and wherein a first slider carries the stylet and the other slider carries the cannula.

Such sliders are associated with hooking/releasing holding devices capable of keeping the same sliders in the wound or axial load position in order to be able to carry out, through controls, two different executions of the removal, namely, a first execution wherein said stylet slider and the cannula slider are released in quick sequence by a single control respectively. The second execution is one in which the stylet slider is released by a first control and the cannula slider is released by a second control.

More particularly, the above mentioned device envisages that hooking/releasing holding means of cannula slider are associated with, and/or co-operating with, the stylet slider, where releasing of the cannula slider holding means occurs and may occur when the stylet slider has reached the end of its advancement stroke only.

This technique presents some substantial drawbacks which vary according to the type of removal to be carried out mentioned hereinafter.

With reference to the first type of removal, that is the one in which the stylet and cannula are advanced in quick sequence, sometimes, in case of a particularly resistant tissue, there may be the inconvenience that execution of the removal is not performed correctly since the stylet slider, not reaching advancement limit stop, does not exert the pressure on cannula slider holding means necessary for their release.

This particular malfunction may cause even serious damage to the patient since it is necessary to move the needle with the stylet partially fed and the cannula backed, that is moving the needle before cannula has made the cut of the sample inside the pierced tissue.

With reference to the second type of removal, that is the one comprising a first stylet advancement by a first control and then a second cannula advancement by a second control, sometimes, in the aforementioned case of particularly resistant tissue, there may be a drawback in that the operator shoots the stylet at first and then, when he presses the push-button for cannula, the release does not occur since the stylet slider, as mentioned above, is not in limit stop position.

OBJECT OF THE INVENTION

It is therefore the object of the present invention to provide a biopsy surgical appliance which overcomes the drawbacks of the prior art.

SUMMARY OF THE INVENTION

According to the invention a biopsy surgical appliance comprising a needle made up of stylet and a cannula coaxially arranged and extending axially along a longitudinal axis with a free end designed to be inserted into the removal area and the other end placed in a handpiece-box containing a device to automatize removal operations by control push-buttons.

The device includes a stylet slider slidingly guided lengthwise inside the handpiece and suitable for carrying and advancing the stylet lengthwise. A cannula slider is slidingly guided lengthwise inside the handpiece and is suitable for carrying and advancing the cannula lengthwise. A first elastic means elastically loads the stylet slider lengthwise. A second elastic means is suitable for elastically loading the cannula slider.

A holding/releasing means is provided to hold the stylet slider and the cannula slider in the wound position to release them in automatic respective quick sequence by a single control or in respective separate sequences by two separate controls. Means is provided for carrying the stylet slider and the cannula slider in the wound position.

The appliance is characterized by the fact that the stylet slider slides in a longitudinal plane arranged laterally with respect to the needle axis and includes a head extending towards and beyond the axis of the needle and suitable for carrying the stylet coaxially with respect to the axis.

The cannula slider slides in a longitudinal plane arranged laterally with respect to needle axis and not interfering in the operative range of stylet slider and includes a head extending towards and beyond the needle axis suitable for carrying the cannula coaxially with respect to the axis.

The releasing/holding means includes a first independent hooking/releasing device for the stylet slider, a second independent hooking/releasing device for the cannula slider, and two independent separate control push-buttons of which the first one acts on the first hooking/releasing and the second one is of the progressive type and acts in progression and the first hooking/releasing device at first if it has not been released yet and then on the second hooking/releasing device.

Through the use of this type of biopsy surgical appliance the release of the slider-carrying cannula occurs also in case the slider carrying the stylet does not reach the limit stop.

With this invention one always succeeds in performing a correct removal of the sample, and by carrying out the removal method in quick sequence the cannula always performs the cutting stroke. By adopting the two-phase removal method the cannula always performs the cutting stroke.

BRIEF DESCRIPTION OF THE DRAWING

Further characteristics and advantages of the invention will be evident from the following description given as a non-restrictive example and made with reference to the drawing wherein:

FIG. 1 is a perspective view illustrating the upper part of a biopsy surgical appliance object according to the invention with the lower part being shown elsewhere;

FIG. 1A is an exploded perspective view illustrating components of biopsy surgical appliance of FIG. 1;

FIG. 1B is a perspective view of the appliance seen in FIG. 1 but without an upper part thereof;

FIG. 2 is a bottom view of the appliance shown in FIG. 1;

FIG. 2A is a sectional view along line IIA—IIA of FIG. 2;

FIG. 3 is a plan view of the appliance shown in FIG. 1;

FIG. 3A is a sectional view along line IIIA—IIIA of FIG. 3;

FIG. 4 is a side view of the appliance illustrated in FIG. 1;

FIG. 4A is a sectional view along lines IVA—IVA of FIG. 4;

FIG. 5 is a plan view of a component of the device of FIGS. 1, 1A and 1B;

FIG. 5A is a section along line VA—VA of FIG. 5;

FIG. 6 is a side view of the appliance shown in FIG. 1A;

FIG. 6A is a sectional view along lines VIA—VIA of FIG. 6;

FIG. 7A is a top schematic view in transparency through an upper wall of the appliance shown in FIG. 1 and illustrating the appliance in an idle state of the load cycle;

FIG. 7B is a sectional top view along the median horizontal plane of the surgical appliance seen in FIG. 7A;

FIG. 7C is a sectional view along line VIIC—VIIC of FIG. 7A;

FIG. 7D is a sectional view along line VIID—VIID of FIG. 7A;

FIG. 8 is a view illustrating an operative detail;

FIG. 9A is a top schematic view in transparency through the upper wall of appliance of FIG. 1 illustrating the appliance in a second position of the load cycle;

FIG. 9B is a sectional view along the horizontal median plane of surgical appliance in the position shown in FIG. 9A;

FIG. 11A is a schematic top view in transparency through the upper wall of appliance case of FIG. 1 illustrating the appliance in a third position of the load cycle;

FIG. 11B is a sectional view along median horizontal plane and from the surgical appliance top in the position seen in FIG. 11A;

FIG. 11C is a sectional view along line XIC—XIC of FIG. 11A;

FIG. 11D is a sectional view along line XID—XID of FIG. 11C;

FIG. 12A is a schematic top view in transparency of the upper wall of the appliance case of FIG. 1 illustrating the appliance in a forth position of load cycle;

FIG. 12B is a sectional view along horizontal median plane and from surgical appliance top in the position shown in FIG. 12A;

FIGS. 13 and 14 are two schematic longitudinal sectional views illustrating a first and second operative phases in the execution of a first type removal aiming at advancing stylet and cannula in quick sequence.

SPECIFIC DESCRIPTION

Figure 9D:
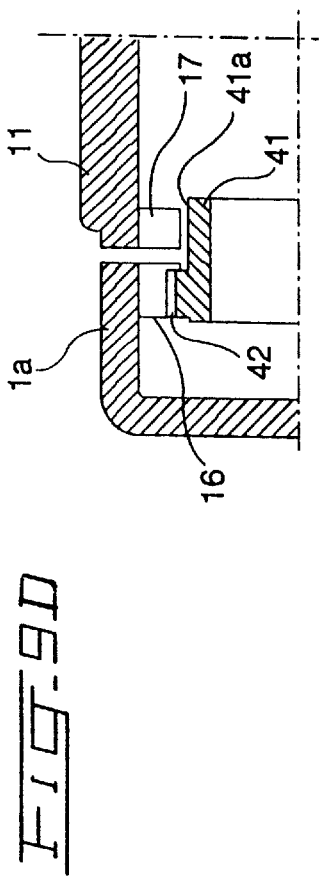
FIG. 9D is a sectional view along line E—E of FIG. 9C.

With reference to FIGS. 1, 1A and 1B, the illustrative appliance extends lengthwise along a y-axis and outside it is made up of a case shaped in two semi-shells 1a and 1b.

Upper shell 1a seen in FIGS. 1–2A is made up of a front wall 2, a side wall 3, a back wall 4, a side wall 5 and an upper wall 6, where front wall 2 includes a semi-hole 7a for the passage of a biopsy needle 8. Upper wall 6 includes a slot 9, a first portion 10 bending in a transversal plane and a second portion 11 bending in a longitudinal plane. An inner surface of wall 6 includes a first longitudinal elevation 12 which configures a longitudinal slicing channel 12a with wall 5, a couple of elevations 13 and 14 which configure a central longitudinal sliding channel 13a between them, a second elevation 15 which configures a longitudinal sliding channel 15a with wall 3, a holding tooth 16, a pushing tooth 17, a holding tooth 18, a pushing tooth 19 and a pushing tooth 10a. The pushing teeth 17 and 19 are carried by bending part 11, and the tooth 10a is carried by bending part 10, so as to be mobile downwards if a force is applied inwards on outer bending part 11 or 10.

The lower shell 1b (FIGS. 1–3A) is formed with front wall 21, a side wall 22, a back wall 23, a side wall 24 and a lower wall 25, where front wall 21 presents a half hole 7b for the passage of needle 8 mentioned above. The lower wall 25 includes a longitudinal elevation 26 which configures a longitudinal sliding channel 26a with wall 24, a double series 27a, 27b, 27c and 28a, 28b, of elevations aligned lengthwise which configure a central sliding channel 27L between them, an elevation 29 which configures a longitudinal sliding channel 29a with wall 22 and, in the center, a passing slot 30.

Inside the shells 1a and 1b a cannula slider 31, a loader slider 32 and a stylet slider 33 slide lengthwise.

The cannula slider 31, FIGS. 4, 4A and 2A, is formed for its guided longitudinal sliding, with a couple of upper flaps 34 and 35 suitable for sliding in the longitudinal channel 12a of upper shell 1a and, below, a couple of flaps 36 and 37 suitable for sliding in the longitudinal channel 26a of lower shell 1b. The four mentioned flaps 34, 35, 36, 37 are carried by a main body 40 having on its top an elastic bridge 41 equipped with a holding mobile tooth 42 and inside the body 40 a back housing 43 and an additional front housing 44 are provided. Housing 43 receives a spring 45 which has its opposite end triggered on a pin 46 equipped with a longitudinal hole 52. The pin 46 is carried by wall 23 of shell 1b and by two shoulders 72 and 73 seen in FIGS. 1A and 7B. The housing 44 houses a spring 70 and spring guide rod 49 with a diameter which is smaller than that of the hole 52 so as to pass through the interspace between the two housings 43 and 44 for the reasons described and explained hereinafter. A front part of the cannula slider 31 includes a head 38 extending transversely beyond y-axis having coaxially with respect to the latter a hole 39 suitable for carrying cannula 80 of needle 8.

With reference to the loader slider 32 (FIGS. 5 and 5A) it slides lengthwise guided in the upper sliding channel 13a of the shell 1a and in the lower guiding channel 27L of shell 1b. The loader slider 32 is provided with a fork central body with tines 47a and 47b, a head 48, spring guiding rod 49 on which spring 70 is triggered, and a couple of wings 50a and 50b suitable for sliding inside respective slots 9 and 30 of shells 1a and 1b.

With reference to head 48, it presents a "U" reversed configuration in which two transversal guides 51a and 51b are made and suitable for carrying a square element 53 sliding transversely and loaded elastically by a sprint 55, which as seen in FIG. 7B stops on a limit stop 69 to inhibit its exit. The square 53, when inserted into guides 51a and 51b has two vertical sides 53s and 53d mobile transversely and respectively destined to selectively meet front faces of cannula slider 32 and stylet slider 33 as better described hereinafter.

The stylet slider 33 (FIGS. 6 and 6A) is formed with a couple of upper flaps 56 and 57 suitable for sliding in the longitudinal channel 15a and, below, a couple a flaps 58 and 59 suitable for sliding in the lower longitudinal channel 29a. The mentioned flaps are carried by a main body 60 having on its top an elastic bridge 61 equipped with a mobile tooth 62 and a housing 63 inside. The housing 63 carries a spring 64 which has its opposed end triggered on a pin 65 carried by the wall 23 of lower shell 1b. The back part of the stylet slider 33 includes a head 66, extending transversely beyond y-axis, which includes a hole 67 that is coaxial with respect to the y-axis in which a stylet back and/or control end 68 of needle 8 is triggered.

With reference to FIGS. 7A, 7B, 7C and 7D, they illustrate the appliance at the beginning of its loading for the subsequent removal, that is in a first idle position.

In the idle position sliders 31, 32 and 33 are pressed on front walls 2 and 21 by the respective springs 45, 70 and 64.

The square 53, sliding transversely to the y-axis, is loaded by spring 55 which presses it on limit stop 69 and, as seen in FIG. 7B, it has two mobile strikers 53s and 53d, of which striker 53s is aligned lengthwise to meet inclined plane 31a of element 31 and striker 53d is aligned lengthwise to meet element 33 front part.

To obtain appliance loading in view of the removal the operator must wind cannula slider 31 first and then stylet slider 33.

The operator acts to move the loader slider 32 backwards by grasping the two wings 50a and 50b extending outside shells 1a and 1b.

With reference to FIG. 8, which illustrates a special operative arrangement, when the loader slider 32 starts moving towards the appliance back part to begin winding or loading operations, striker 53s interferes with inclined plane 31a thus entailing a displacement of the relative square 53 on the left, so that striker 53d does not interfere with element 33 front part.

Figure 9C:
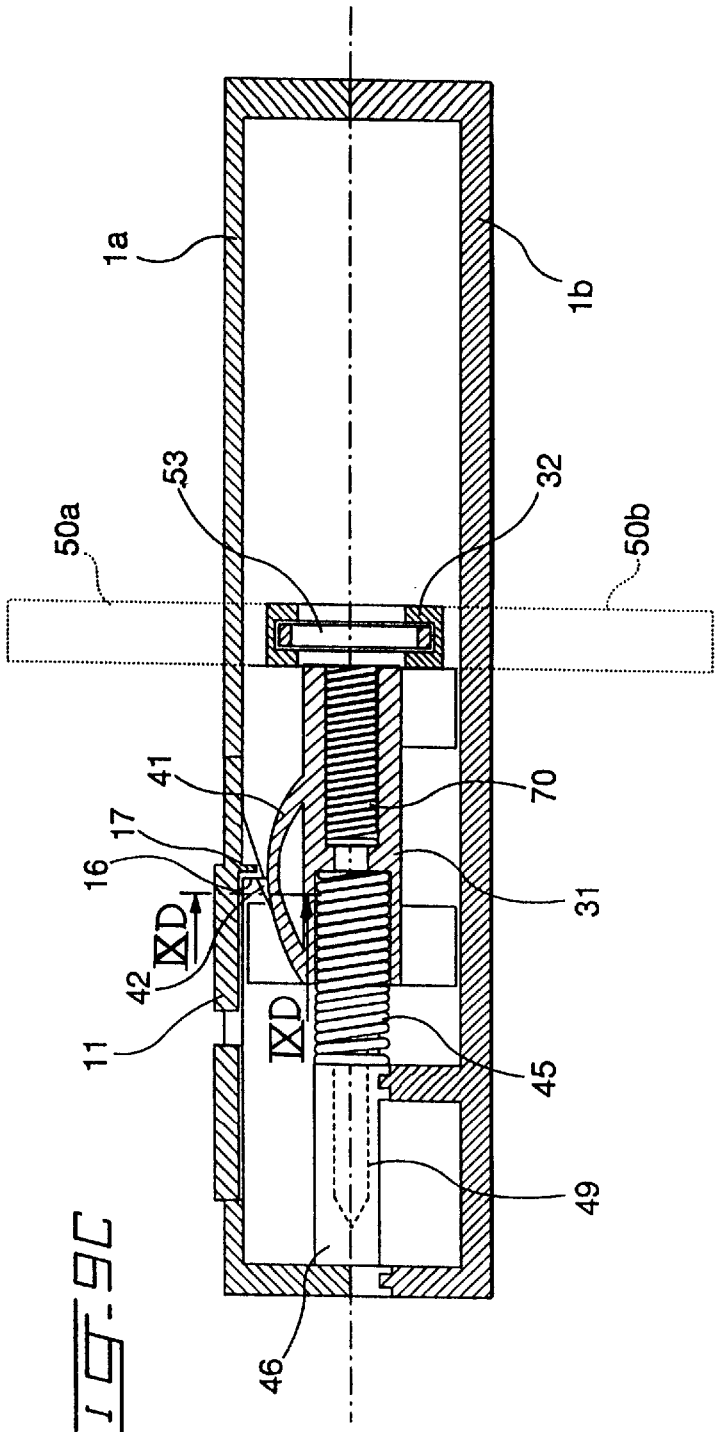
FIG. 9C is a sectional view along line C—C of FIG. 9A.

With reference to FIGS. 9A, 9B and 9C, the loader slider 32 has been pulled backwards and it has dragged cannula slider 31 with itself. The cannula slider, moving backwards, has compressed spring 45 and mobile holding tooth 42, carried by elastic bridge 41, and hooking fixed holding tooth 16 carried by shell 1a. With reference to this hooking, see FIGS. 9C and 9E, please note that mobile holding tooth 42 clutches with fixed tooth 16 and that bridge 41 includes an upper portion 41a, extending lengthwise and arranged transversely at the tooth side 42, which is aligned vertically with pushing tooth 17 carried by bending part 11, so that, by pressing the bending part 11, pushing tooth 17 presses on bridge 41 and as it is pressed down it is lowered with subsequent release of teeth 16 and 42 for the reasons described hereinafter.

Figure 10A:
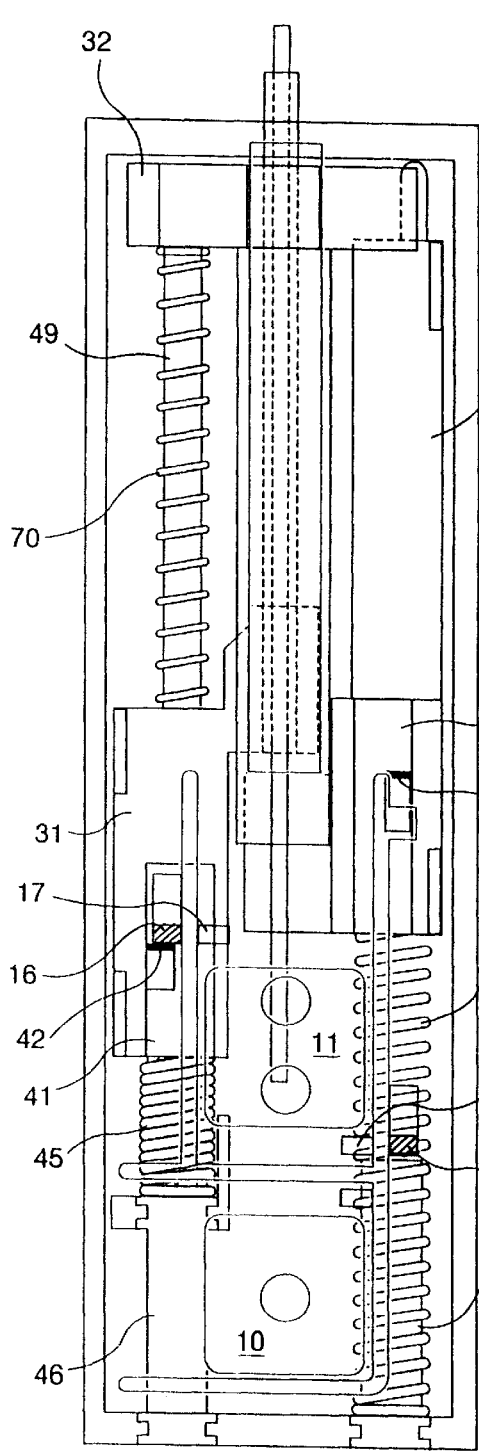
FIG. 10A is a top schematic view in transparency through the upper wall of appliance of FIG. 1 illustrating the appliance in a third position of load cycle.
Figure 10B:
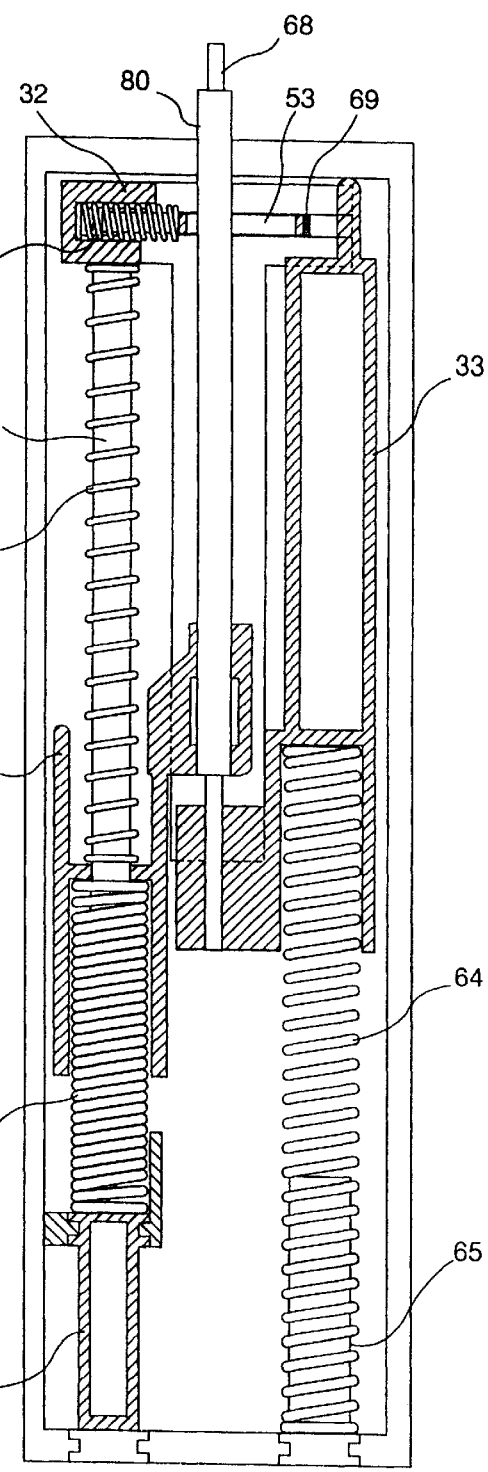
FIG. 10B is a sectional view along median horizontal plane and from surgical appliance top in the position illustrated in FIG. 9A.

With reference to FIGS. 10A and 10B, loader slider 32 after loading cannula slider 31 as mentioned above, returns to the former position by pushing spring 70 while square 53 loaded by spring 55 positions on limit stop 69.

With reference to FIGS. 11A, 11B and 11D, loader slider 32 has been pulled again towards the back and has dragged stylet slider 33 with itself. In this respect please note that since cannula slider 31 is positioned towards the back, square 53 is not subject to transversal displacements by inclined plane 31a.

Stylet slider 33, moving backwards, has compressed spring 64 and mobile holding tooth 62, carried by elastic bridge 61, has hooked fixed holding tooth 18 carried by shell 1a. With reference to that hooking (FIG. 11E) please note that mobile holding tooth 62 clutches with fixed tooth 18 and that bridge 61 includes an upper portion 61a, extending lengthwise and arranged transversely at tooth side 62, which is aligned vertically with pushing tooth 19 carried by bending part 11, so that, by pressing said bending part 11, presses on tooth 19 pushes bridge 61 and as it is pressed down it is lowered with subsequent release of teeth 62 and 18 for the reasons described hereinafter.

Figure 12D:
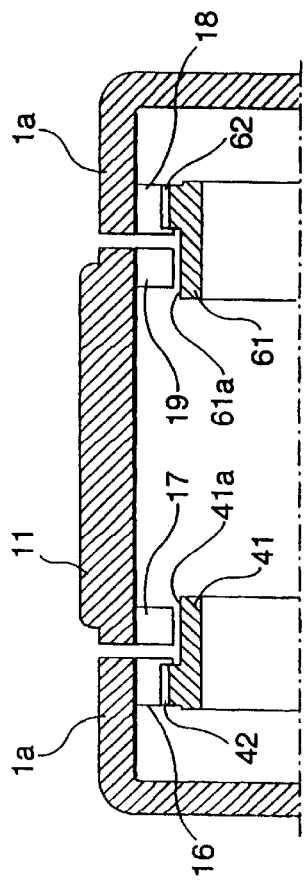
FIG. 12D is a sectional view along line XIID—XIID of FIG. 12C.
Figure 12C:
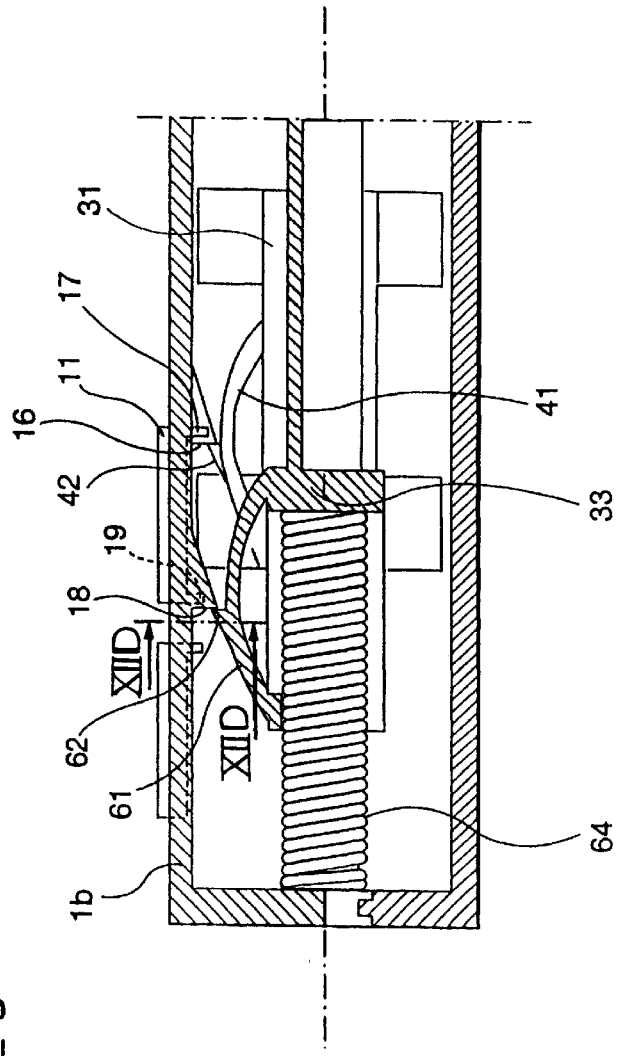
FIG. 12C is a sectional view along plane XIIC—XIIC of FIG. 12A.

With reference to FIGS. 12A and 12B, loader slider 32 after loading stylet slider 33 as mentioned above, returns to its former position by pushing spring 70.

After executing the above-mentioned winding operations (FIGS. 12D and 12E) the stylet slider 33 is wound and held in position through hooking of teeth 18–62 while cannula slider 31 is wound and held in position through hooking 42-16. Furthermore, bending part 11 has two pushing teeth 19 and 17 where pushing tooth 19 can press elastic bridge 61 of cannula slider 33 in order to release it and pushing tooth 17 can press elastic bridge 41 of stylet slider 31 to release it.

With reference to the type of removal to be performed, the operator must wind the appliance as described above first and then insert needle 8 in the tissue and position its free point in the area destined to removal.

At this point the operator may opt for two different types of removal, a first type where the stylet 68 and the cannula 80 are advanced in successive quick sequence by a single control, or a second type of removal where stylet 68 is advanced by a first control and cannula 80 by a second control.

With reference to first type of removal (FIGS. 13D and 14D) the operator, applying a strength directed from outside to inside on bending element 11, moves pushing teeth 19 and 17 downwards with different movements, where tooth 19 during bending phase executes downwards movements which are greater with respect to tooth 17.

More particularly, flexure of bending element 11 entails first stylet slider 33 release through pushing tooth 19 pressure on bridge 61 which involves mobile holding tooth 62 to be released from fixed holding tooth 18 with subsequent advancement of stylet slider 33 by pre-wound spring 64 (FIG. 13D). Then, due to further flexure of bending element 11, it entails mobile holding tooth 42 release from fixed holding tooth 16 with subsequent advancement of cannula slider 31 by pre-wound spring 45 as shown in FIG. 14D.

In such a manner advancement of stylet 68 and cannula 80 is obtained in quick sequence as required for first type of removal, and in case stylet 68 and therefore the relative slider 33 because of a particularly hard tissue do not reach advancement limit stop, cannula 80 executes its cutting stroke all the same since the release of the holding means 42-16 is independent from the system relative to stylet slider 33.

Figure 15:
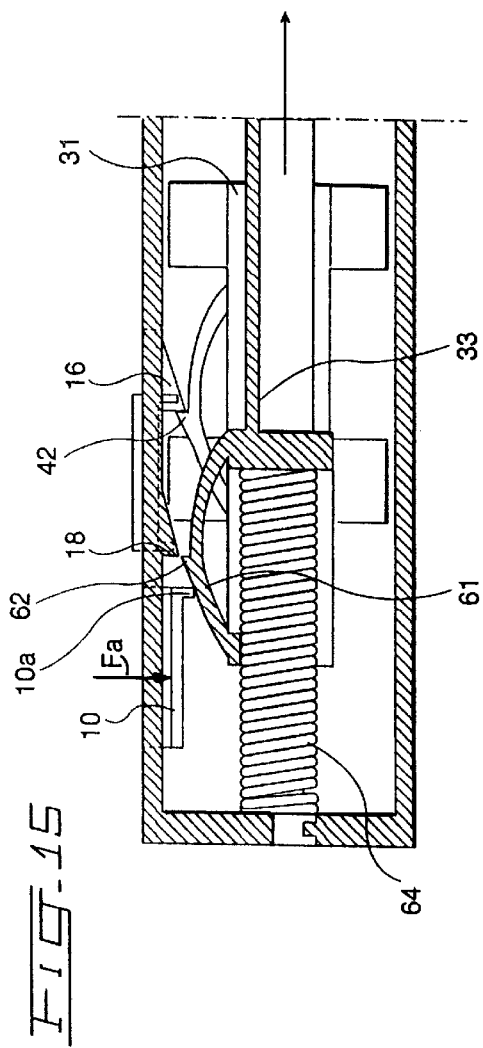
FIGS. 15 and 16 are two sectional longitudinal schematic views illustrating a first operative phase and a second operative phase in the execution of a removal of the type aiming at advancing the stylet by a first control and the cannula by a second control.
Figure 16:
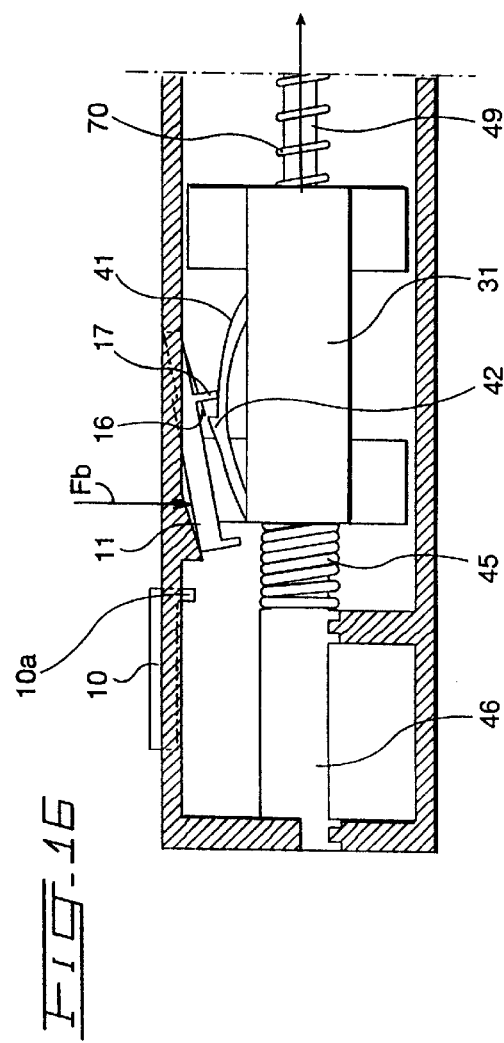

With reference to second type of removal (FIGS. 15D and 16D) the operator, applying a first control through a first strength FA directed from outside to inside on the bending element 10, moves bridge 61 downwards through pushing tooth 10a, thus entailing the release of holding tooth 62 from holding tooth 18 with subsequent advancement of stylet slider 33 by pre-wound spring 64, see FIG. 15D. Then, after examining the correct arrangement of needle point 8 by magnetic resonance, computed axial tomography or other systems, the second control is operated through the application of a strength FB on bending element 11 by releasing cannula slider 31 as aforementioned.

In such a manner advancement of cannula 80 is obtained also in case slider 33, because of a particularly hard tissue found stylet point 68, does not reach advancement limit stop, since the release of the holding means 42-16 of cannula slider 31 are not associated with stylet slider 33.

The description of the above mentioned appliance is given as a non-restrictive example and thus it is evident that any modification or variation may be introduced into it according to practice and its use or employment and however within the scope of the following claims.

I claim:

1. A biopsy instrument comprising:
    an elongated housing;
    a first slider in said housing biased by a first spring toward an end of said housing for driving a stylet into tissue to be sampled, said first slider having first detent means for releasably retaining said first slider in a retracted position;
    a second slider in said housing alongside said first slider and biased by a second spring toward said end of said housing for driving a cannula coaxially surrounding said stylet into said tissue, said second slider having second detent means for releasably retaining said second slider in a retracted position;
    a first control pushbutton formed on said housing for deflecting one portion of a wall thereof to release said first detent means and propel said first slider toward said end; and
    a second control pushbutton on said housing for deflecting another portion of said wall thereof to first release said first detent means and then release said second detent means and propel said first and second sliders toward said end in succession when said first detent means has not been previously released and to release said second detent means to propel said second slider toward said end when said first detent means has previously been released by said first control pushbutton.

2. The instrument defined in claim 1, further comprising a head longitudinally displaceable in said housing and having a pair of arms projecting through longitudinal slots in opposite walls of said housing for retracting said slides against force of said springs to re-engage said first and second detent means.

3. The instrument defined in claim 2 wherein said head has a transversely shiftable member engageable with said first slider and spring-biased towards said first slider.

4. The instrument defined in claim 1 wherein one of said portions of said wall is deflectable transversely and the other of said portions of said wall is deflectable longitudinally with respect to a longitudinal axis of said housing.

5. The instrument defined in claim 1 wherein each of said detent means includes a bowed spring on the respective slider carrying a tooth projecting toward said wall.

6. The instrument defined in claim 2 wherein a further spring is provided between said head and said second slider.

7. The instrument defined in claim 1 wherein said wall is provided with teeth cooperating with said first and second detent means.

8. The instrument defined in claim 1 wherein said housing is formed with guides for said slides.

9. The instrument defined in claim 8 wherein said guides are ribs projecting from a wall of said housing opposite the wall provided with said portions.

10. A biopsy surgical assembly comprising:
    a housing extending along a longitudinal axis;
    an elongated cannula extending axially outwardly from the housing along the axis and terminating away therefrom;
    an elongated stylet extending coaxially with and through the cannula and terminating away from the housing and the cannula, actuating means for controllably displacing the cannula and stylet to remove a tissue to be examined and comprising:
        a first and second longitudinal guides spaced laterally in opposite directions from the axis in the housing,
        a stylet slider displaceably received in the first guide and formed with a respective head extending laterally toward and terminating beyond the axis and displacing the stylet in a plane including said longitudinal axis between respective axial retracted and extended positions,
        a cannula slider displaceably received in the second guide and formed with a respective head extending toward and terminating beyond the axis and displacing the cannula in said plane between respective retracted and extended axial positions,
        first elastic means for bringing the stylet in the respective retracted position,
        second elastic means for bringing the cannula slider in the respective retracted position, and
        means for holding the stylet and cannula sliders in the respective retracted positions and for sequentially releasing them in automatic sequence through a single control or in respective separate sequence by two separate controls, the releasing means comprising:
            first hooking means
                for engaging the stylet slider in the respective inner position,
            second hooking means
                for engaging the cannula slider in the respective inner position, and
            a pair of independent
                separate control push-buttons operatively connected with the first and second hooking means,
        one of the buttons acting upon the first hooking means to release the stylet slider for reaching the tissue to be examined by the stylet in the respective extended position, and
        the other of the buttons sequentially disengaging the first and second hook means thereby first releasing the stylet slider and thereafter the cannula slider if the stylet has not reached the tissue upon actuating of the one button.

11. The assembly defined in claim 10 wherein the housing is formed with two halves, each of the first and second elongated guides being a respective pair of channels formed respectively in each of the halves and lying in a respective common plan upon bringing the halves together, the stylet slider including:
    an elongated body received in the halves and formed with:
        two pairs of axially spaced flaps guided along the respective pair of channels formed in the halves, and
        an elastic bridge facing one of the halves and formed with a respective tooth extending toward the one half;

the cannula slider including an elongated body received
in the halves and formed with:
- two pairs of axially spaced flaps guided along the respective pair of channels formed in the halves, and
- an elastic bridge facing the one half and formed with a respective tooth extending toward the one half, each of the first and second hooking means being formed with:
- a respective tooth formed on the one half and extending inwardly to the other half and adapted to engage the respective teeth of the stylet and cannula sliders respectively in the respective retracted positions thereof, said teeth being disengaged upon actuating the push buttons.

12. The assembly defined in claim 11 wherein said push buttons are formed on the one half and each has a respective bending portion displaceable inwardly toward the other half upon actuation.

13. The assembly defined in claim 10 further comprising a loader slider selectively engaging each of said stylet and cannula sliders and formed with a pair of wings extending in opposite directions transversely to said axis and terminating away from said housing, the loader slider being formed with a respective elastic means including a spring for providing a return stroke thereof in a respective extended position upon terminating of a load stroke of the loader slider bringing said styler and cannula sliders in the respective retracted positions.

14. The assembly defined in claim 13 wherein said loader slider is further formed with:
- a respective body,
- engaging means for selectively engaging each of said styler and cannula sliders during the load stroke of the load slider, and
- an elongated guide rod receiving the spring and slidable axially in the cannula slider to wound the spring for the return stroke upon bringing said stylet and cannula sliders in the respective retracted positions.

* * * * *